(12) United States Patent
Squibb

(10) Patent No.: US 9,833,643 B2
(45) Date of Patent: Dec. 5, 2017

(54) APPARATUS FOR PROVIDING CONTROLLED FLOW OF INHALATION-AIR

(71) Applicant: Mark Squibb, Bellvue, CO (US)

(72) Inventor: Mark Squibb, Bellvue, CO (US)

( * ) Notice: Subject to any disclaimer, the term of this patent is extended or adjusted under 35 U.S.C. 154(b) by 0 days.

(21) Appl. No.: 14/663,881

(22) Filed: Mar. 20, 2015

(65) Prior Publication Data

US 2015/0314145 A1 Nov. 5, 2015

Related U.S. Application Data

(60) Provisional application No. 61/974,699, filed on Apr. 3, 2014.

(51) Int. Cl.

| | | |
|---|---|---|
| *A61M 15/00* | (2006.01) | |
| *A61M 16/00* | (2006.01) | |
| *A62B 7/00* | (2006.01) | |
| *A62B 7/10* | (2006.01) | |
| *A62B 9/00* | (2006.01) | |
| *A62B 18/00* | (2006.01) | |
| *A62B 23/02* | (2006.01) | |
| *A62B 9/02* | (2006.01) | |
| *A61M 16/10* | (2006.01) | |
| *A61M 16/20* | (2006.01) | |
| *A62B 18/02* | (2006.01) | |

(52) U.S. Cl.
CPC .......... *A62B 7/10* (2013.01); *A61M 16/0045* (2013.01); *A61M 16/107* (2014.02); *A61M 16/204* (2014.02); *A62B 9/02* (2013.01); *A62B 23/02* (2013.01); *A62B 23/025* (2013.01); *A62B 18/02* (2013.01)

(58) Field of Classification Search
CPC .... A62B 7/00; A62B 7/10; A62B 7/12; A62B 16/20; A62B 16/201; A62B 16/204; A62B 7/02; A62B 27/00
See application file for complete search history.

(56) References Cited

U.S. PATENT DOCUMENTS

| | | | | |
|---|---|---|---|---|
| 3,441,020 A | * | 4/1969 | Aasen .................... | A61M 16/06 128/205.25 |
| 4,121,578 A | * | 10/1978 | Torzala ................. | A61M 16/12 128/204.22 |
| 4,427,056 A | * | 1/1984 | Johnson ............... | B60H 1/0065 137/625.48 |

(Continued)

OTHER PUBLICATIONS

Handout from Exhibition event (2012)—showing applicant's company name and website www.extremeo2.com.

*Primary Examiner* — Kristen Matter
(74) *Attorney, Agent, or Firm* — Robert DeWitty

(57) ABSTRACT

Disclosed is an apparatus for providing controlled flow of inhalation-air from at least an air-reservoir to a mask. The apparatus includes a control unit and a switch unit. The control unit controls the level of the inhalation-air flowing from the air-reservoir to the mask. The control unit includes a housing to receive the inhalation-air from the air-reservoir, plurality of ducts protruding from the housing to connect with the air-reservoir and with the mask and a valve configured to control the flow of inhalation-air from the plurality of ducts. The switch unit positions a valve to selectively open and close the plurality of ducts for regulating the flow of inhalation-air from the air-reservoir to the housing.

14 Claims, 7 Drawing Sheets

(56) References Cited

U.S. PATENT DOCUMENTS

| | | | | |
|---|---|---|---|---|
| 5,261,457 A | * | 11/1993 | Zapata | A61M 16/20 137/625.65 |
| 7,955,294 B2 | * | 6/2011 | Stenzler | A61M 16/0051 128/203.12 |
| 2006/0144396 A1 | * | 7/2006 | DeVries | H02P 6/17 128/204.21 |

* cited by examiner

APPARATUS FOR PROVIDING CONTROLLED FLOW OF INHALATION-AIR

CROSS REFERENCE TO RELATED PATENT APPLICATION

The present invention claims priority of the provisional patent application No. 61/974,699 filed on Apr. 3, 2015; all of which are incorporated herein by reference in their entireties.

BACKGROUND OF THE INVENTION

1. Field of the Invention

The present invention generally relates to an apparatus for providing inhalation-air from dual compartment air-reservoir to a mask, and more particularly relates to an apparatus for switching in between a high concentration of oxygen and a contrasting low concentration of oxygen to provide selected concentration of oxygen a user.

2. Description of Related Art

Events that reduce the dissolved oxygen concentration in blood plasma induce adverse changes in health status. These changes are richly documented in the book Oxygen Multistep Therapy, by Manfred von Ardenne, herein included by reference, with a specific discussion of a vascular inflammatory mechanism within the first chapter, Physiological Mechanisms.

Short-term reductions in blood plasma oxygen concentration often cause endothelial inflammation, to create persistent, and often permanent vascular constrictions. These reductions often follow chemical, physical or emotional stress events. These constrictions reduce blood and oxygen delivery to downstream tissue causing tissue distress, disease vulnerability and accelerated degeneration.

Long-term reduction in plasma oxygen deprives avascular cells structures, like cartilage, ligaments, white blood cells, and lens of the eye, of oxygen, resulting in reduced elasticity, performance and healing capacity of avascular structures, including the vascular system itself. These plasma hypoxia conditions remain unrecognized and hence an inactionable cofactor in many disorders.

Prior art systems utilize single air mixture, with a fixed oxygen partial pressure to administer extra oxygen to the body. Ardenne disclosed multiple methods of administering extra oxygen during physical challenge to increase the oxygen partial pressure of the respiratory mixture by using a fixed oxygen partial pressure in continuous delivery flow.

Ardenne also disclosed use of physical challenge as, exercise, heat, or pharmaceutical adrenal analogue to simultaneously up-regulate respiratory turbulence, as heart rate, and respiratory tidal volume. Increased respiratory turbulence caused more oxygen to dissolve in blood plasma resulting in a collection of methods to treat a plurality of health conditions that occurred as a consequence of blood plasma hypoxia.

Ardenne disclosed a fixed rate of supplemental oxygen during exercise ranging from 2-3 liters per minute to 50 liters per minute for athletes. It is known that for able-bodied individuals elevated rates of supplemental oxygen prevent the body from achieving maximum respiratory turbulence, and hence less than maximum achievable dissolved plasma oxygen.

Prior art systems that supply a fixed amount of extra oxygen during exercise increases oxygenation to only about half of what is achievable with the invention. The fixed elevation in oxygen partial pressure caused a net decrease in respiratory turbulence because extra oxygen makes it easier for the mammal's heart and lungs to meet respiratory demand.

This reduction in respiratory turbulence limits tissue perfusions because maximum heart rate and maximum arterial dilation are required to deliver maximum pulse pressure to capillaries. Exemplary tissue perfusion reflects the force of blood pumped by the heart, and the ability of oxygen enriched plasma to squirt past narrowed vascular narrow areas resulting from endothelial inflammation or injury.

The exemplary performance of the invention occurs when the mammal achieves a novel respiratory status of simultaneous maximum pulse and maximum oxygen partial pressure. This state is specifically induced when the briskly exerting mammal switches from a respiratory challenge status, respiratory mixture with reduced oxygen partial pressure, to respiratory recovery status, with a mixture with maximum oxygen partial pressure.

The novel exemplary effect occurs when the exerting mammal achieves simultaneous maximums of respiratory turbulence while breathing a mixture of maximum oxygen partial pressure. This occurs just after the switch from low oxygen partial pressure to high oxygen partial pressure. These moments, while the exerting mammal experiences of maximum heartbeat, with elevated oxygen partial pressure, create optimal conditions for tissue oxygen perfusion unachievable by any known prior art system.

These maximums are indicated by novel simultaneous physiological maximums: maximum oxygen tidal volume, maximum pulse rate, maximum oxygen partial pressure in the respiratory mixture, maximum force of blood in the venous structure, hypoxia induced vasodilation, all serve to create maximum force of blood pressure at the capillary entry, and hence maximal tissue blood perfusion for the mammal. It should be obvious to the skilled in the art that these simultaneous maximum conditions are unachievable by any prior art system due to the usage of single air concentration.

The novel achievement of these maximums produce rapid physiological effects from improved blood flow to organ systems and muscles throughout the body measured with pharmacological tests including mental performance. Therefore there is a need of an apparatus that reproduce physiological improvements disclosed by Ardenne, normally occurring in 36 hours using oxygen multistep methods, in approximately 15 minutes or less while providing two different concentrations of oxygen.

Further, the apparatus should provide more intense and more cumulative physiological improvements than those disclosed with prior art systems. Further, the apparatus should increase the testing of human athletic capacity increases dramatically and rapidly.

Many prior art systems utilize varying rates of oxygen delivery, but do not disclose use of contrasting air mixtures. There are three classifications of prior art systems, Oxygen Multistep, which delivers a fixed increase in oxygen partial pressure during exercise; hyperbaric which delivers a fixed level increased oxygen partial pressure at rest to the whole body; and hypoxic training systems that deliver a reduced partial pressure of oxygen at rest or during exercise to induce durable adaptive change for improved general oxygen utilization.

The key to dealing with blood plasma oxygen deficiency is to utilize the body's adaptive response to progressively contrasting altitudes. There have been various attempts at providing portable chambers that simulates different altitude to show the effects of increased altitude, and/or to obtain some of the advantages of simulating different altitudes for, e.g., athletic training. It has been used to train athletes for the purpose of improved athletic performance, pre-acclimatization to altitude and/or physical wellness.

In hypoxic chambers and exercise systems, the occupant is subjected to lower oxygen partial pressure such as to simulate high altitudes. It is well known to expose an exerting mammal to hypoxic conditions utilizing a respiratory mixture with a reduced oxygen partial pressure. This exposure creates beneficial vascular conditions known to improve distal tissue oxygenation. The beneficial effect normally occurs when a mammal adapts hypoxic conditions, which causes hypoxic vasodilation, and other effects.

Simultaneous hypoxic vasodilation with exertion causes increased pulse pressure at the capillary that squirts more blood through capillaries than normal. This enhanced pulse pressure improves tissue perfusion. The challenge in hypoxic exertion however, is that the blood plasma contains less oxygen than normal due to the reduced oxygen in the respiratory mixture. This reduction generally prevents oxygen dissolved the blood plasma from acting as an endothelial anti-inflammatory, as disclosed by Ardenne, and may provoke additional inflammation.

It should be apparent to one skilled in the art that the exemplary aspect of the invention utilizes hypoxic conditions to establish the hypoxic vasodilation to establish maximum pulse pressure at the capillary, and then switches to a maximal oxygen partial pressure, to change from the reduced oxygen plasma oxygen partial pressure available with prior art hypoxic training systems, to an enhanced oxygen partial pressure by the increased oxygen partial pressure.

This switch condition creates exemplary and novel conditions at the distal tissue, which are unachievable by non-switching hypoxic training systems that solely utilize a reduced oxygen partial pressure, or even during the recovery process when the exerting mammal recovers from the hypoxic training by recovering to normal air. The exemplary aspect of the invention utilizes the vascular conditions created by hypoxic exertion, immediately followed by enhanced oxygen. It should be apparent to one skilled in the art that the invention is therefore novel with respect to all forms of hypoxic training systems, and chambers.

Another type of simulation system includes hyperbaric chambers and are used in the medical and sports industries. In essence, occupants of hyperbaric chambers undergo hyperbaric treatments in which they are subjected to relatively high oxygen partial pressures. Hyperbaric treatments are known, amongst other things, to enhance muscular recuperation and to increase dissolved oxygen levels in body fluids.

Conventional hyperbaric chambers are typically made of rigid materials capable of withstanding pressure differentials. Accordingly, hyperbaric treatments are not commonly accessible and are often only available to elite-level athletes and selected patients.

However, prior art portable chambers have some shortcomings relative to the invention. Hyperbaric sessions have a physically slow response time, normally requiring 40 or more hours of use to produce a clinically measurable result. With the invention, equivalent, and usually superior results are achieved normally within about 3 minutes for able bodied users.

Hyperbaric chambers require whole body pressurization which often causes inner ear discomfort with most users. Physical encapsulation also causes claustrophobia for many users. Medical grade hyperbaric chambers require materials that cause them to cost at least 20× the amount of the invention. Medical hyperbaric administration requires one or two trained operators for safe administration health challenged individuals in a medical or professional context. Therefore, there is need of an apparatus to provide an enhanced form of exercise which is safe and easy to use for anyone capable of virtually any form of stationary exercise and does not require an administrator and can be used safely at home.

Hence, despite ongoing developments in the field of hyperbaric chambers, hypoxic breathing systems, and fixed mixture exercise with oxygen systems, there remains a need for a respiratory delivery system to create optimal physiological conditions for maximum oxygen partial pressure in blood plasma, and consequently tissue oxygen perfusion. This combination provides exemplary mitigation capacity of health conditions relating to plasma hypoxia, and inhibited tissue oxygen perfusion, and hence provides novel capacity to overcome shortcomings of prior art portable chambers used for hyperbaric and/or hypoxic treatments. These systems do not utilize rapidly switchable contrasting oxygen partial pressures of the invention. It should be apparent to one skilled in the art that prior art systems do not alone, or any practical combination, create the novel vascular conditions of the invention.

Accordingly, it would be desirable to have a more cost effective apparatus for providing controlled flow of inhalation-air from an air-reservoir to a mask that could better simulate contrasting altitudes, and in particular, easily simulate both lower and higher altitudes than the current altitude of a person. Further, the apparatus should be portable and should be set up at any place.

SUMMARY OF THE INVENTION

The present invention provides an apparatus for providing controlled flow of inhalation-air from an air-reservoir to a mask and the air-reservoir having a first air chamber to store a first concentration of the inhalation-air, and a second air chamber to store a second concentration of the inhalation-air.

In the preferred embodiment, the exemplary difference in oxygen partial pressures between the chambers ranges from maximum oxygen concentration exceeding 42% up to 95%, with a reduced oxygen concentration reduced at least 20% to 60% below normal oxygen partial pressure.

An object of the present invention is to provide an apparatus including a control unit and a switch unit. The control unit switches the source of inhalation-air flowing from the reservoir to the mask to change from oxygen rich to oxygen reduced air, to provide a contrasting oxygen partial pressure of the inhalation-air.

This mechanism enables the user to exert using a high respiratory challenge level to achieve maximum pulse and respiratory challenge, and then switch to rich oxygen to utilize respiratory inertia with enhanced oxygen level to achieve maximum plasma oxygen saturation, and maximum physically achievable tissue oxygen perfusion.

The control unit includes a housing to receive the inhalation-air from the air-reservoir, plurality of ducts protruding from the housing to connect with the air-reservoir and with the mask. The first duct is configured with the first air chamber to supply the first concentration of inhalation-air to the housing.

The second duct configured with the second air chamber to supply the second concentration of inhalation-air to the housing, and a third duct to transfer the received inhalation-air by the housing from the air-reservoir to the mask. The control unit further includes at least one valve configured to control the flow of inhalation-air from the first duct and the second duct to the housing.

Furthermore, the switch unit positions the valve to selectively open and close the first duct and the second duct for regulating the flow of inhalation-air from the air-reservoir to the housing.

Additionally, the switch unit includes a cable to move the valve to selectively open and close the first duct and the second duct for regulating the flow of inhalation-air from the air-reservoir to the housing and a mechanical switch having a first position to actuate the cable to set the position of the valve for receiving the inhalation-air from the first duct; and a second position to actuate the cable to set the position of the valve for receiving the inhalation-air from the second duct.

The switch unit further includes a solenoid to move the valve to selectively open and close the first duct and the second duct and an electrical switch having a first position to actuate the solenoid to set the position of the valve for receiving the inhalation-air from the first duct; and a second position to actuate the solenoid to set the position of the valve for receiving the inhalation-air from the second duct.

The apparatus further includes plurality of filter units attached to each duct to filter the inhalation-air passing to the user.

Furthermore, the housing includes a first strip attached on right side of the second duct to maintain the position of the valve, a second strip in between the first duct and the second duct to maintain the position of the valve, a third strip attached on right side of the first duct to maintain the position of the valve.

Another object of the present invention is to provide an apparatus for altitude contrast training of a user. The apparatus includes an air-reservoir, a mask, a control unit, a switch unit and one or more tubular conduits. The air reservoir includes a first air chamber to store a first concentration of inhalation-air, a second air chamber to store a second concentration of inhalation-air and a seam to separate the high-concentration chamber from the low-concentration chamber.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

Figure 1:
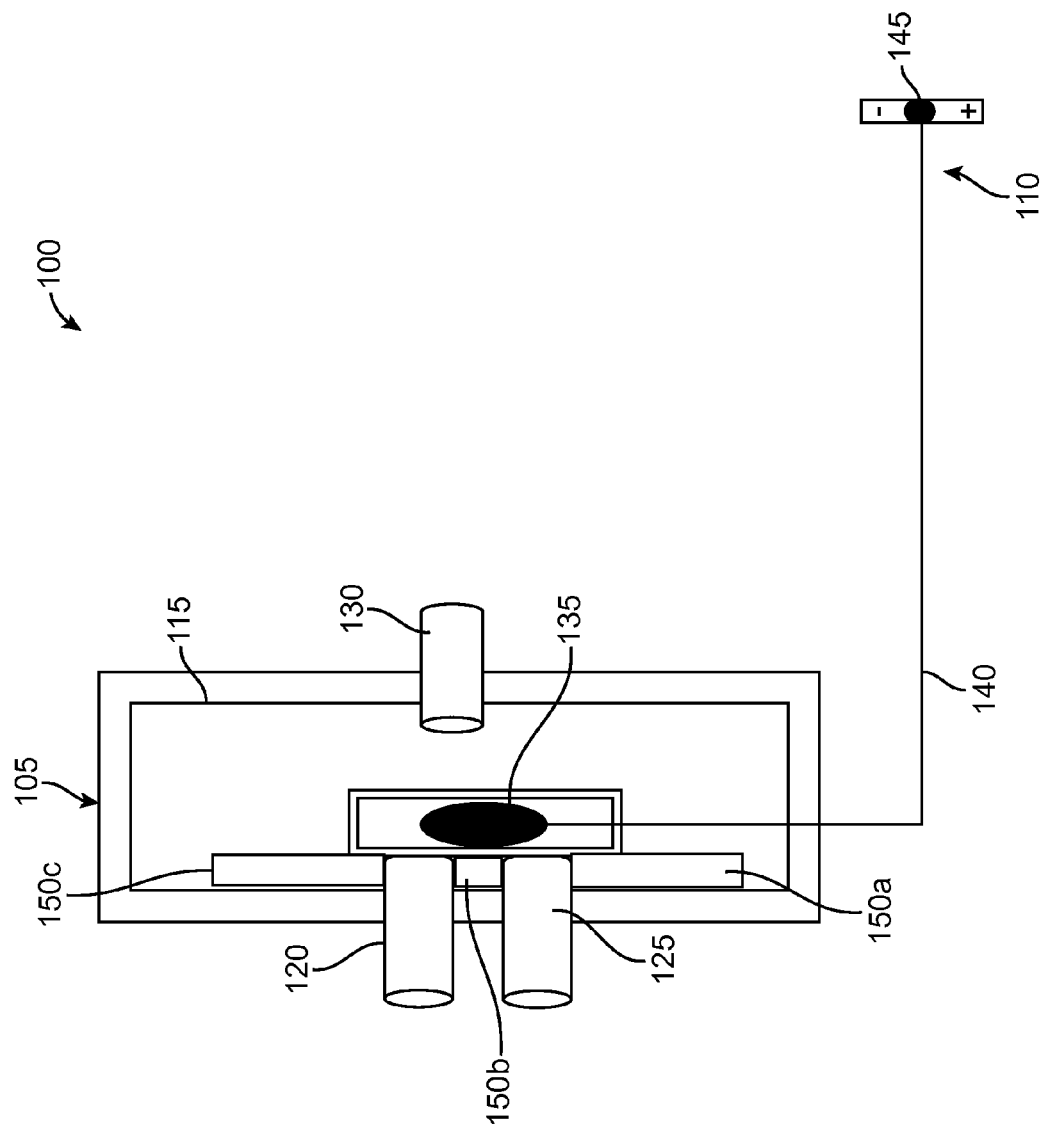
FIG. 1 illustrates a schematic diagram of an apparatus for providing controlled flow of inhalation-air, in accordance with a preferred embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE DRAWING

While this technology is illustrated and described in a preferred embodiment, an apparatus for providing controlled flow of inhalation-air from at least an air-reservoir to a mask of a user may be produced in many different configurations, forms and materials. There is depicted in the drawings, and will herein be described in detail, as a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the technology described herein.

Reference will now be made in detail to several embodiments of the invention which are illustrated in the accompanying drawings. Wherever feasible and convenient, the same reference numerals are used in the figures and the description to refer to the same or like parts. The drawings are in a simplified form and not to precise scale. For purposes of convenience and clarity only, directional terms, such as top, bottom, left, right, up, down, over, above, below, beneath, rear, and front may be used with respect to the accompanying drawings.

These and similar directional terms should not be strictly construed to limit the scope of the invention. In addition, words such as attached, affixed, coupled, connected and similar terms with their inflectional morphemes are used interchangeably, unless the difference is noted or made otherwise clear from the context. These words and expressions do not necessarily signify direct connections, but include connections through mediate components and devices.

FIG. 1 illustrates a schematic block diagram of an apparatus 100 for providing controlled flow of inhalation-air from the air-reservoir (not shown in FIG. 1) in accordance with a preferred embodiment of the present invention. The air-reservoir having a plurality of air chambers, a first air chamber to store a first concentration of the inhalation-air; and a second air chamber to store a second concentration of the inhalation-air. The air chambers are explained in detail in conjunction with FIG. 2 to FIG. 4 of the present invention.

The apparatus 100 includes a control unit 105 and a switch unit 110. The control unit 105 controls the flow of the inhalation-air, further the control unit 105 receives air from the air-reservoir (not shown in FIG. 1) and transfers the inhalation-air to the user. The switch unit 110 positions the control unit 105 to selectively receive at least one of the inhalation-air from at least one of the air chambers (not shown in FIG. 1) of the air-reservoir.

In a preferred embodiment of the present invention, the control unit 105 includes a housing 115 to receive the inhalation-air from the air-reservoir (not shown in FIG. 1), plurality of ducts such as a first duct 120, a second duct 125, and a third duct 130 protruding from the housing 115 to connect with the air-reservoir and with the user; and at least one valve 135 to control the flow of inhalation-air from the first duct 120 and the second duct 125 to the housing 115. The first duct 120 is configured with the first air chamber (explained in detail in conjunction with FIG. 3A) to supply the first concentration of inhalation-air to the housing 115.

The second duct 125 is configured with the second air chamber (explained in detail in conjunction with FIG. 3B) to supply the second concentration of inhalation-air to the housing 115. The third duct 130 is configured to transfer the received inhalation-air by the housing 115 from the air-reservoir (not shown in FIG. 1) to the mask (not shown in FIG. 1).

The valve 135 is configured to control the flow of inhalation-air from the first duct 120 and the second duct 125 to the housing 115. Examples of the valve 135 include but not limited to magnetic valves, air-actuated ball valves, and motorized ball valves, lead screw or linear actuator positioned flapper valves, or other valves configurations. It would be readily apparent to those skilled in the art that various types of the valves 135 may also be envisioned to control the flow of inhalation-air without deviating from the scope of the invention.

The control unit 105 further includes at least one valve 135 configured to control the flow of inhalation-air from the first duct 120 and the second duct 125 to the housing 115. The third duct 130 transfers the inhalation-air from the housing 115 to the mask through a tubular conduit (explained in detail in conjunction with FIG. 2).

In a preferred embodiment of the present invention, the control unit 105 switches the source of inhalation-air flowing from the air-reservoir to the mask to change from oxygen rich to oxygen reduced air, to provide a contrasting oxygen partial pressure of the inhalation-air. This mechanism enables the user to exert using a high respiratory challenge level to achieve maximum pulse and respiratory challenge, and then switch to rich oxygen to utilize respiratory inertia with enhanced oxygen level to achieve maximum plasma oxygen saturation, and maximum physically achievable tissue oxygen perfusion.

The apparatus 100 includes a switch unit 110 to position the valve 135 to selectively open and close the first duct 120 and the second duct 125 for regulating the flow of inhalation-air from the air-reservoir (not shown in FIG. 1) to the housing 115. The position of the valve 135 is explained in detail in conjunction with FIG. 3A and FIG. 3B of the present invention.

The switch unit 110 further includes a cable 140 and a mechanical switch 145. The cable 140 moves the valve 135 to selectively open and close the first duct 120 and the second duct 125 for regulating the flow of inhalation-air from the air-reservoir to the housing 115.

The mechanical switch 145 having a first position (explained in detail in conjunction with FIG. 3A) actuates the cable 140 to set the position of the valve 135 for receiving the inhalation-air from the first duct 120 and a second position (explained in detail in conjunction with FIG. 3B) to actuate the cable 140 to set the position of the valve 135 for receiving the inhalation-air from the second duct 125.

Examples of mechanical switch 145 includes but not limited to toggle switch, rocker switch, double pole switch, slide switch, rotary switch, key switch and tilt switch. It would be readily apparent to those skilled in the art that various type of the switch unit 110 may also be envisioned to switch the flow of inhalation-air without deviating from the scope of the invention. In a preferred embodiment of the present invention, the switch unit 110 may be operated mechanically by the user.

In another preferred embodiment of the present invention, the switch unit may include a solenoid and an electrical switch. The solenoid moves the valve to selectively open and close the first duct and the second duct. The electrical switch may have a first position to actuate the solenoid to set the position of the valve for receiving the inhalation-air from the first duct and a second position to actuate the solenoid to set the position of the valve 135 for receiving the inhalation-air from the second duct 125.

Examples of electrical switch include but not limited to a motor in electrical connection with a source of electrical current and a direct current backup battery or other power storage device may be provided for positioning the valve 135.

In another preferred embodiment of the present invention, the housing 115 includes a first strip 150a attached on right side of the second duct 125 to maintain the position of the valve 135, a second strip 150b in between the first duct 120 and the second duct 125 to maintain the position of the valve 135 and a third strip 150c attached on right side of the first duct 120 to maintain the position of the valve 135 with the housing 115.

Examples of the first strip 150a, second strip 150b and the third strip 150c includes but not limited to a magnetic strip, mechanical constraints or any other retaining units. However it would be readily apparent to those skilled in the art that various types of the strips 150 may be used to maintain the position of the valve 135 without deviating from the scope of the invention.

Figure 2:
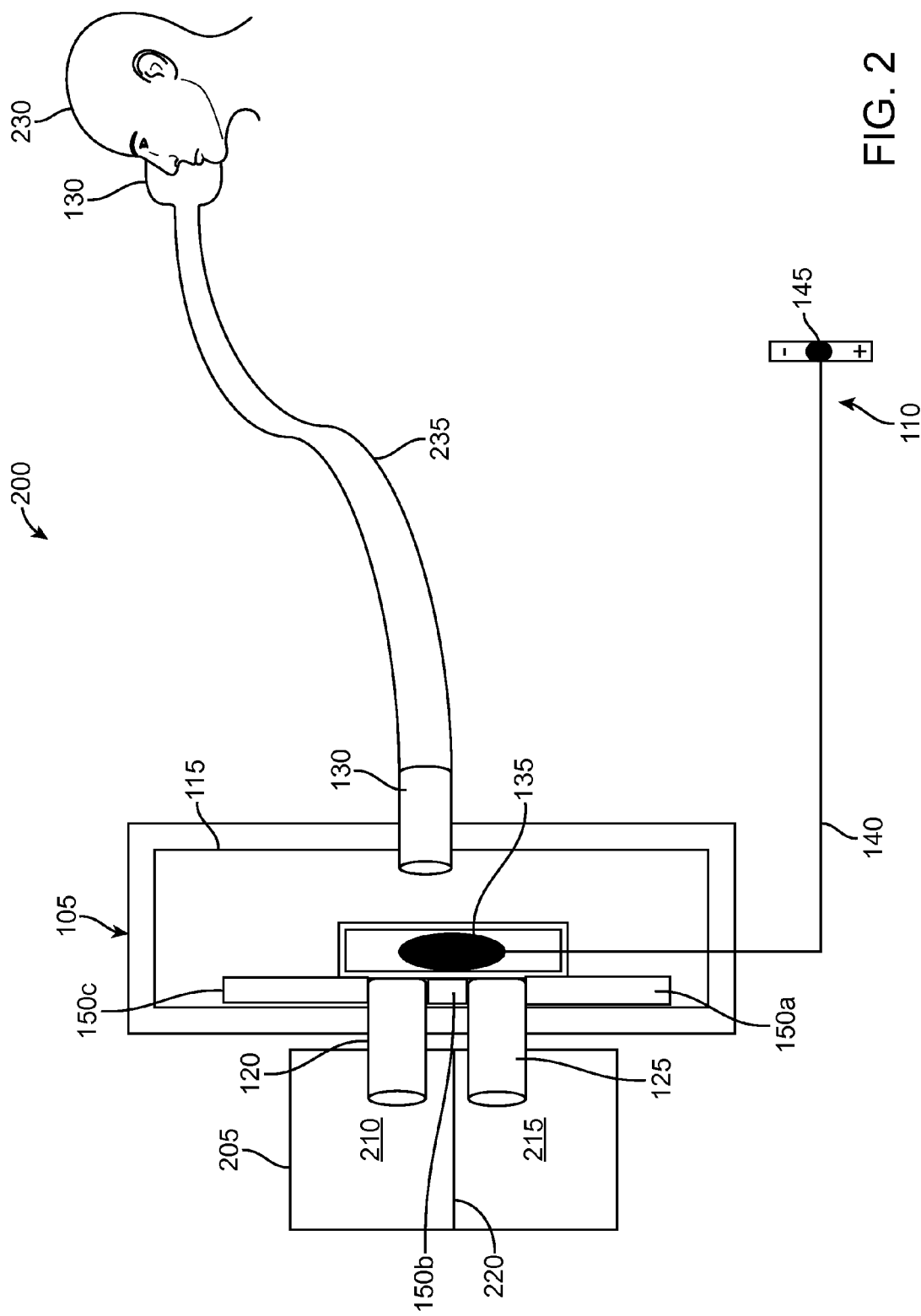
FIG. 2 illustrates a schematic diagram of an apparatus for providing controlled flow of inhalation-air from at least an air-reservoir to a mask, in accordance with another preferred embodiment of the present invention.

FIG. 2 illustrates the schematic block diagram of an apparatus 200 for providing altitude contrast training to a user 230 in accordance with another preferred embodiment of the present invention. The apparatus 200 includes an air-reservoir 205 to store inhalation-air, a mask 225, a control unit 105, and a tubular conduit 235.

The air-reservoir 205 includes a first air chamber 210 to store a first concentration of inhalation-air, a second air chamber 215 to store a second concentration of inhalation-air, and a seam 220 separating the first air chamber 210 from the second air chamber 215. The apparatus 200 may be particularly suited for use with an inhalation-air such as oxygen, nitrous oxide, medical air, carbon dioxide, helium, nitrogen, any other breathing gases etc. The first concentration of inhalation-air is the high concentration inhalation-air and the second concentration of inhalation-air is the low concentration inhalation-air.

In an exemplary embodiment the air-reservoir 205 may include a physically separate first air chamber 210 and a second air chamber 215 to store a first concentration of inhalation-air and a second concentration of inhalation-air respectively. In another exemplary embodiment the air-reservoir 205 may have first air chamber 210 physically contained within the second air chamber 215.

In a preferred embodiment of the present invention, the air-reservoir 205 is made of a flexible material that expands to store the inhalation-air. The inhalation-air is filled in the air-reservoir 205 by an external-air-source such as oxygen concentrator. The interior portion of the air-reservoir 205 is made of a medical grade or food grade membrane impervious to the contained inhalation-air (no plasticizers that give off chemicals) and the outer portion is made of durable, scuff resistant dust cover. However, it would be readily apparent those skilled in the art that various types of materials may be used to create air-reservoir 205 without deviating from the scope of the present invention.

Further, the air-reservoir 205 may be formed of a low-oxygen-permeability-material for accumulating the inhalation-air in an undiluted form. The air-reservoir 205 may be available in several sizes. Examples of the size of air-reservoir 205 may be around 1000 L capacity, 1500 L capacity etc. However, it would be readily apparent to those skilled in the art that various sizes of the air-reservoir 205 may be envisioned without deviating from the scope of the present invention. Typically, the air-reservoir 205 may be hung on the wall or any handy frame work nearby the work station.

In an exemplary embodiment, the difference in oxygen partial pressures between the chambers ranges from maximum oxygen concentration exceeding 42% up to 95%, with a reduced oxygen concentration reduced at least 20% to 60% below normal oxygen partial pressure. However, it would be readily apparent to those skilled in the art that various concentrations of inhalation-air in the air-reservoir 205 may be envisioned without deviating from the scope of the present invention.

The mask 225 transfers the inhalation-air from the air-reservoir 205 to the user 230 for facilitating breathing. The mask 225 may be worn by the user 230 at the time of exercise e.g. cycling and may be made of plastic, silicone, or rubber. In a preferred embodiment of the present invention, the mask 225 may cover the nose and mouth (oral nasal mask) or the entire face (full-face mask) of the user 230.

The mask 225 may have a one way valve to breathe the inhalation-air in and may have a separate one way valve to breathe out into the atmosphere. However, it would be readily apparent to those skilled in the art various types of mask 225 such as nose cannula may be envisioned to deliver the inhalation-air to the user 230 without deviating from the scope of the invention.

The control unit 105 (explained in detail in conjunction with FIGS. 3A and 3B) controls the level of the inhalation-air flowing from the air-reservoir 205 to the mask 225 through the tubular conduits 235. The switch unit 110 is operated by the user 230 for positioning the valve 135 to selectively open and close the first duct 120 and the second duct 125 for regulating the flow of inhalation-air from the air-reservoir 205 to the housing 115 (explained in detail in conjunction with FIGS. 3A and 3B). However, it would be readily apparent to those skilled in the art that other users may also be able to operate the switch unit 110 without deviating from the scope of the present invention.

Further, the tubular conduit 235 allows the flow of inhalation-air from the housing 115 to the mask 225. The tubular conduit 235 may be of any dimension and may be made of plastic, silicone, or rubber. The tubular conduit 235 may be of several feet to allow the air-reservoir 205 to be positioned further away from the exercise equipment. Typically, the tubular conduit 235 delivers the oxygen in the range of 10-100 Liters per minute.

In an exemplary embodiment, the switch unit 110 includes a mechanical switch 145 which is at a neutral position. The valve 135 is attached to the second strip 150b and thus closes the path of the inhalation-air to flow through the first duct 120 and the second duct 125. Therefore no inhalation-air is flowing from the air-reservoir 205 to the housing 115.

In another embodiment, the valve 135 may be operative to vary the ratio of the first concentration of inhalation air with the second concentration of inhalation air in such a way that the concentration of inhalation air in the housing 115 is in between the first concentration of inhalation-air and the second concentration of inhalation-air.

Figure 3A:
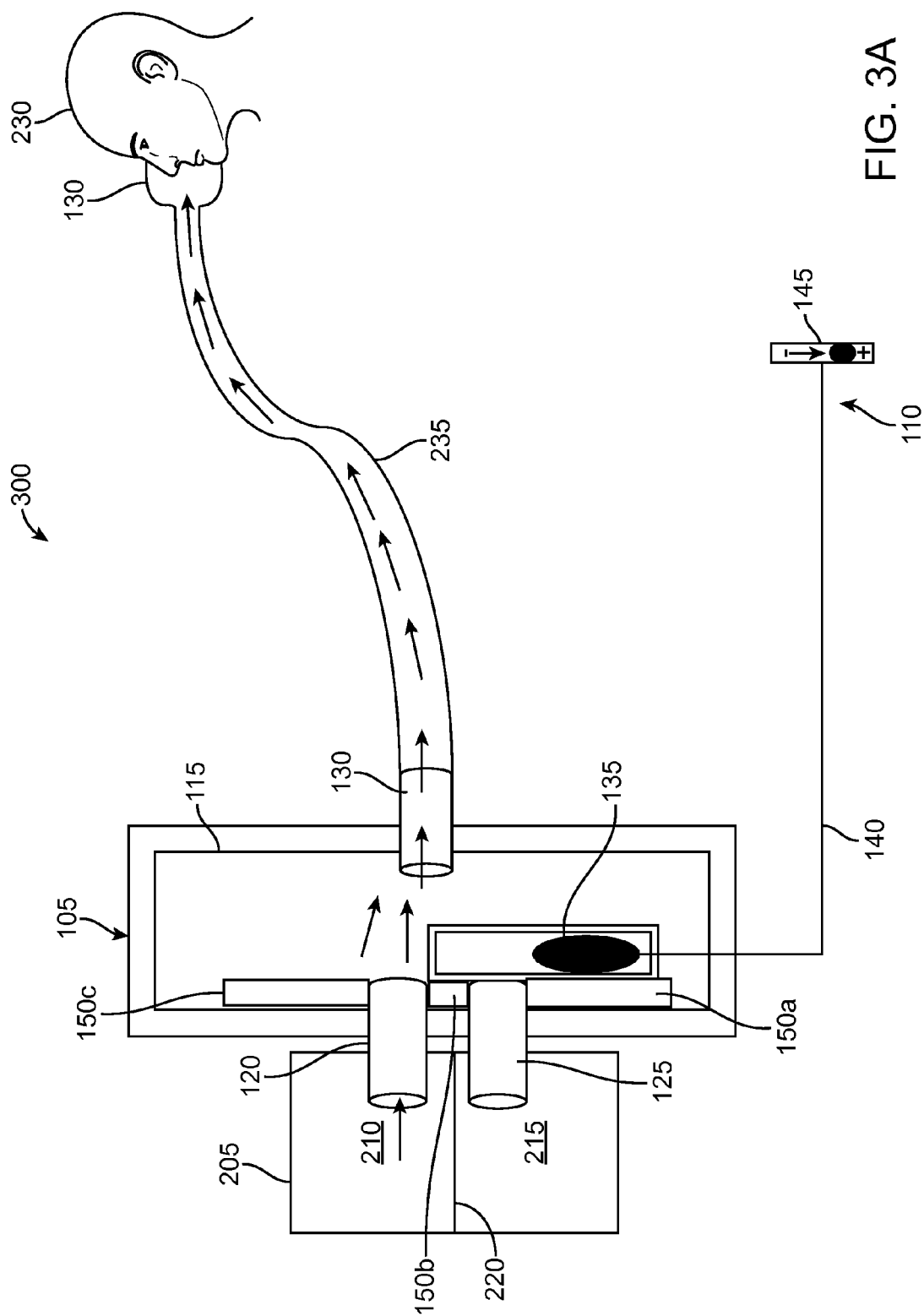
FIG. 3A illustrates the schematic diagram of an apparatus for providing controlled flow of the first concentration of inhalation-air from the first air chamber to the user, in accordance with a preferred embodiment of the present invention.
Figure 3B:
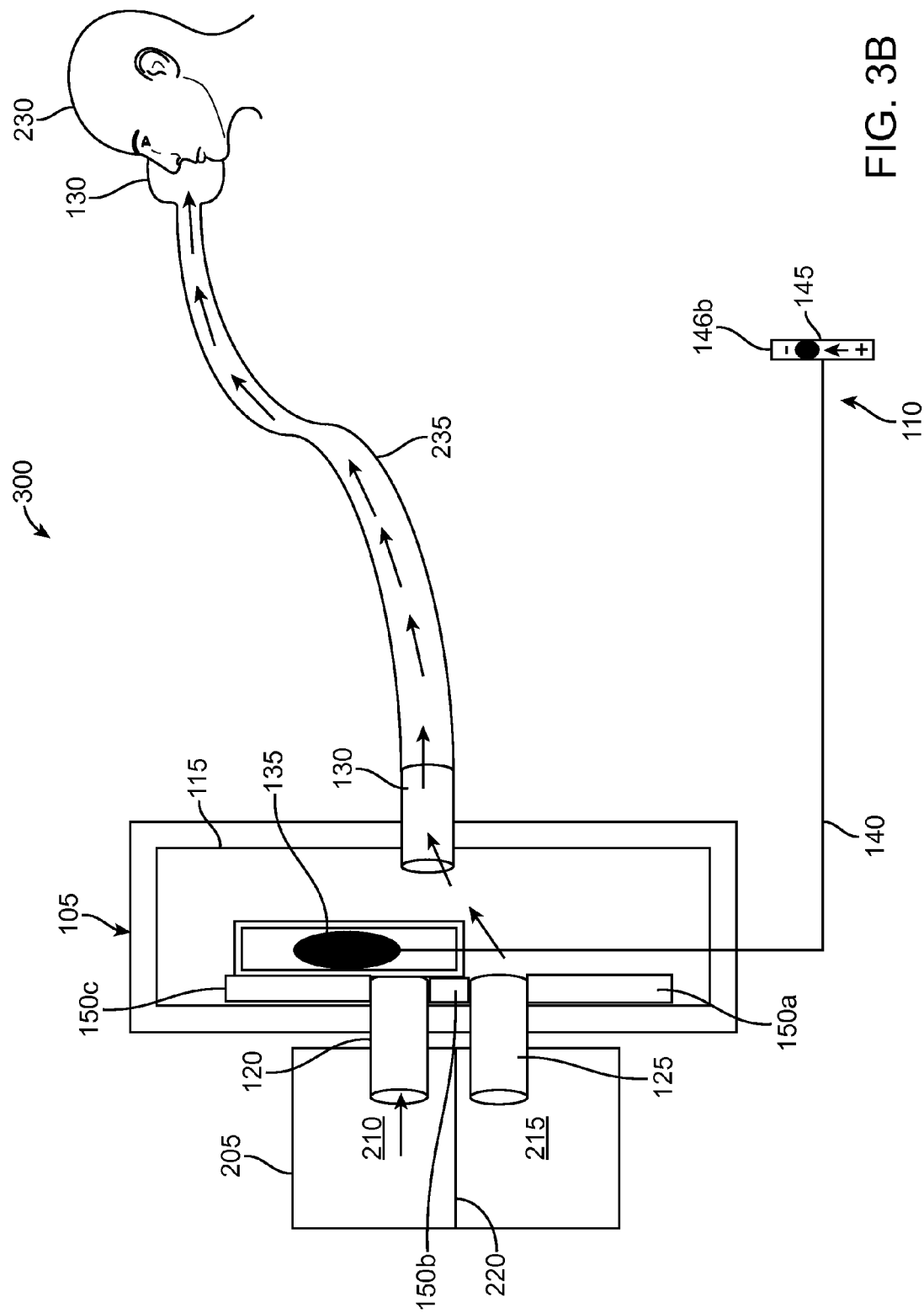
FIG. 3B illustrates the schematic diagram of an apparatus for providing controlled flow of the second concentration of inhalation-air from the second air chamber to the user, in accordance with a preferred embodiment of the present invention.

FIGS. 3A and 3B illustrates the schematic block diagrams of an apparatus 300 for providing controlled flow of the first concentration of inhalation-air from the first air chamber 210 and the second concentration of inhalation-air from the second air chamber 215 to the user 230 respectively, in accordance to the preferred embodiment of the present invention.

In a preferred embodiment of the present invention, the first concentration of inhalation-air is the high concentration of the oxygen at or above 20.9% at the sea level. Similarly, the second concentration of inhalation-air is low concentration of oxygen at or below 20.9% at the sea level. The low concentration of oxygen is roughly equivalent to the amount of oxygen available at the high altitudes but any oxygen concentration lower than ambient air is anticipated by the present invention.

In an exemplary embodiment as shown in FIG. 3A, the mechanical switch 145 is at a first position 146a for receiving the first concentration inhalation-air from the first air chamber 210 by the housing 115 through the first duct 120. The mechanical switch 145 pulls back the cable 140 to position the valve 135 against the second duct 125.

The valve 135 is attached to the first strip 150a and the second strip 150b and thus closes the path of the inhalation-air to flow through the second duct 125 from the second air chamber 215. Similarly as shown in FIG. 3B, the mechanical switch 145 is at a second position 146b for receiving the second concentration inhalation-air from the second air chamber 215 by the housing 115 through the second duct 125.

The mechanical switch 145 pushes the cable 140 to position the valve 135 against the first duct 120. The valve 135 is attached to the second strip 150b and third strip 150c and thus closes the path of the inhalation-air to flow through the first duct 120 from the first air chamber 210. Thus, the desired inhalation-air is then made to flow out of the housing 115 to the user 230 through the third duct 130, the tubular conduit 235 and the mask 225.

The aforementioned switching of the high concentration of the inhalation-air to the low concentration of the inhalation-air allows the user 230 to experience the physiological adaptations. It may help to restore two hormone cycles that fades with age i.e. erythropoietin (EPO) and human growth hormone (HGH). EPO triggers creation of red blood cells (RBC) which carry oxygen to the tissues.

Low concentration inhalation-air may cause hypoxic stress and may signal the body to increase EPO up to 1000 times to adapt to hypoxic challenge. HGH is an anabolic hormone that controls structural growth of bones and muscles. It is the main hormone of youth, and high levels are keys to both graceful aging and athletic performance. The apparatus 300 of the present invention helps the user in increasing HGH levels over 500%.

Figure 4:
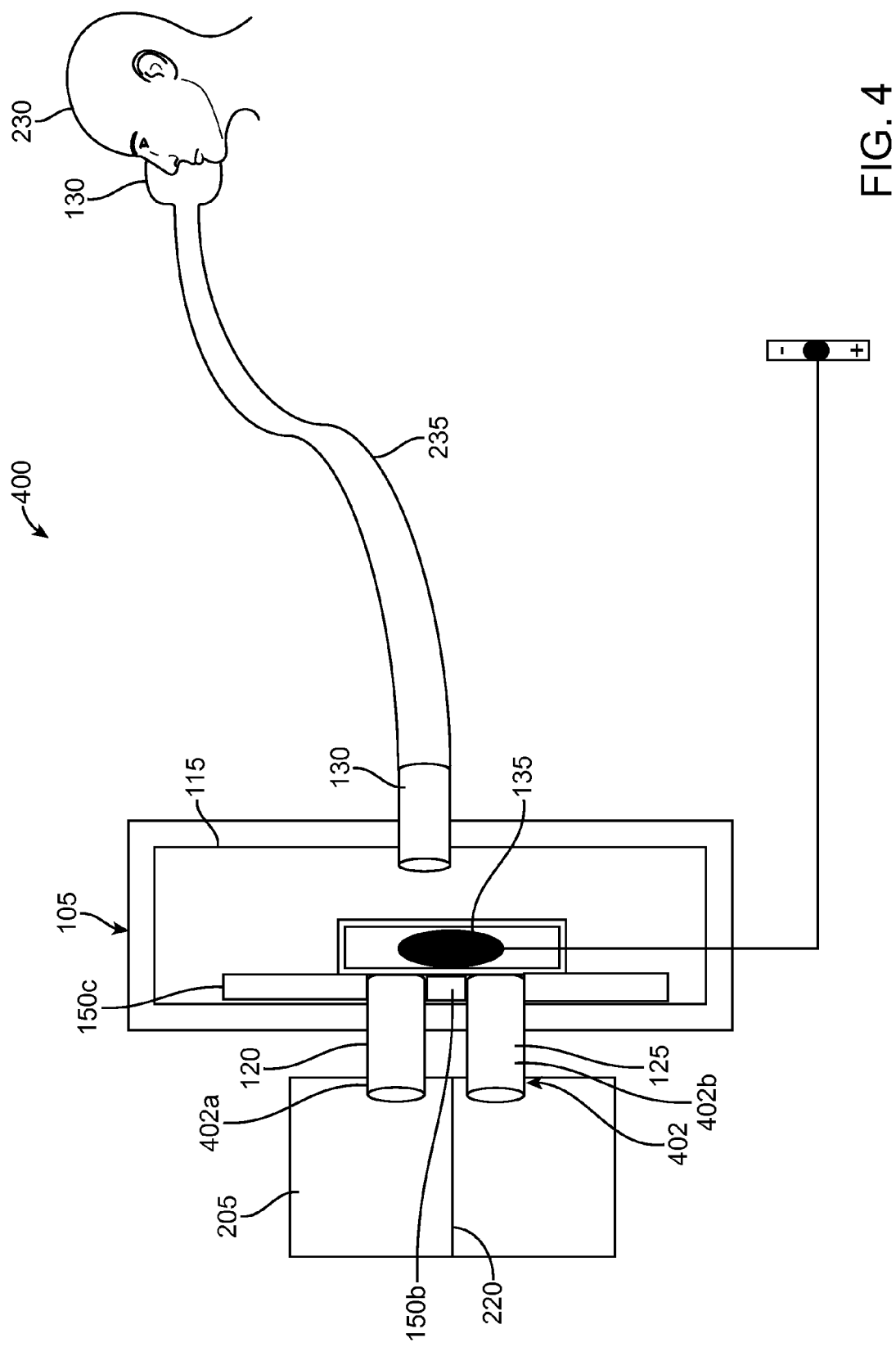
FIG. 4 illustrates the schematic diagram of an apparatus for showing filter units, in accordance with a preferred embodiment of the present invention.

FIG. 4 illustrates the schematic block diagrams of an apparatus 400 for showing filter units 402. The apparatus 400 includes plurality of filter units 402 such as a first filter unit 402a and a second filter unit 402b attached to the first duct 120 and the second 125 respectively. The filter units 402 transfers the filtered inhalation-air received from the air-reservoir 205 to the housing 115. The filtered air is then transferred to the user 230 from the housing 115.

The filter units 402 may remove unwanted particulates from the inhalation-air such as airborne molecular contaminants etc. Examples of the filter unit 402 include but not limited to a cassette filter having sides of wire net, paper, carbon, foam, or cotton filters and spun fiberglass filter. The inhalation-air that is passed through the plurality of filter units 402 may pass through the filter textile from the air-reservoir 205 into the housing 115.

Figure 5:
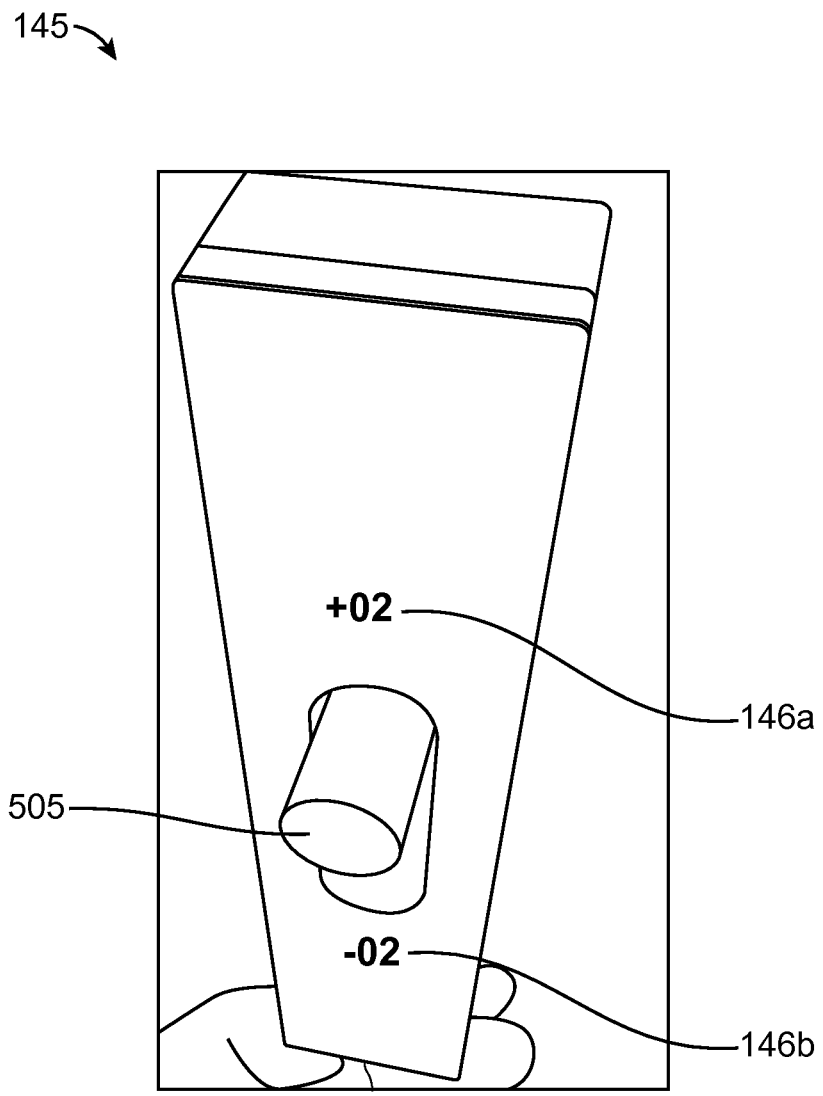
FIG. 5 illustrates the schematic diagram of a mechanical switch, in accordance with a preferred embodiment of the present invention.

FIG. 5 illustrates the schematic diagram of a mechanical switch 145. The mechanical switch 145 includes a slide button 505. The slide button 505 is moved linearly to and fro to set the first position 146a i.e. +02 and the second position 146b i.e. −02 respectively and actuates the cable (not shown in fig.) to set the position of the valve for receiving the inhalation-air from the first duct or from the second duct (explained in detail in conjunction with FIG. 3A and FIG. 3B respectively).

In another preferred embodiment of the present invention, though not shown in figures, the apparatus includes a noise suppression unit to suppress the noise produced during the filling of inhalation-air in the air-reservoir.

Figure 6:
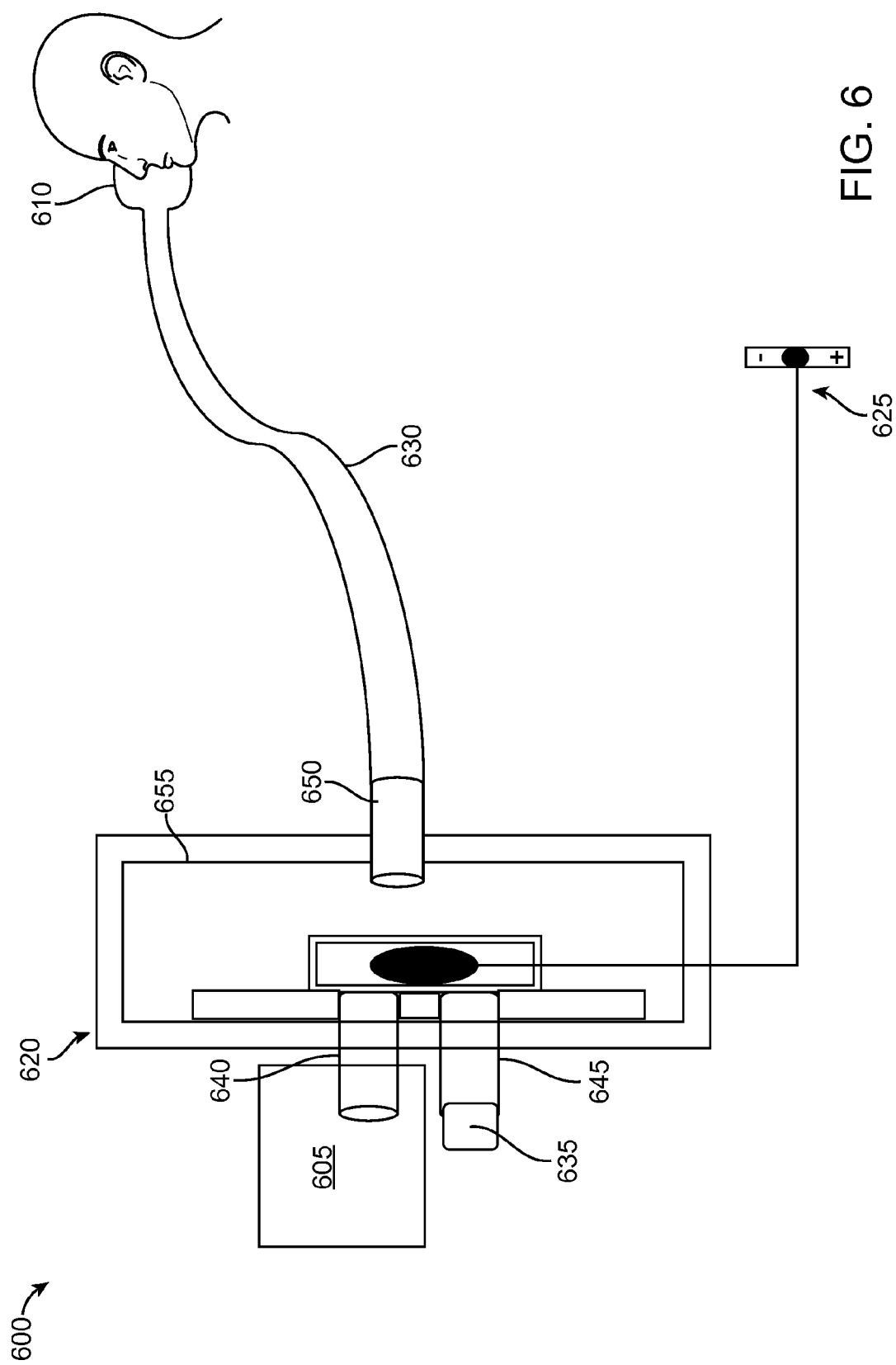
FIG. 6 illustrates the schematic diagram of an apparatus for controlled flow of inhalation-air, in accordance with another preferred embodiment of the present invention.

FIG. 6 illustrates the schematic diagram of an apparatus 600 for showing a stop-valve 635 in accordance with another preferred embodiment of the present invention. The apparatus 600 includes an air-reservoir 605, a mask 610, a control unit 620, a switch unit 625, one or more tubular conduit 630 and a stop-valve 635.

The air-reservoir 605 stores a high concentration inhalation-air. Further, the mask 610 transfers the inhalation-air to the user for facilitating breathing. The control unit 620 controls the flow of inhalation-air from the air-reservoir to the mask 610 (explained in detail in conjunction with FIG. 1 where the control unit 620 has the same functionality as the control unit 105 explained in FIG. 1).

The control unit includes a first duct 640 configured with the air reservoir 605 to supply the high concentration inhalation-air to the housing 655, and a second duct 645 to transfer low concentration of inhalation-air from the atmosphere to the housing 655, and a third duct 650 to transfer the received inhalation-air by the housing 655 to the mask 610.

The apparatus 600 includes a switch unit 625 (explained in detail in conjunction with FIG. 1 where the switch unit 110 has the same function as the switch unit 625). The one or more tubular conduits 630 are explained in detail in conjunction with FIG. 2 and the one or more tubular conduits 630 has same function as tubular conduit 235. The apparatus 600 includes a stop-valve 635 to control the flow of the air from the second duct 645.

The present invention offers various advantages as it allows switching of the position of the valve to allow release of selective inhalation-air from the air-reservoir. This principle is utilized in restoring the blood flow, accelerate tissue regeneration, improve physical performance, improve fluid intelligence, disease avoidance, disease recovery. The apparatus is useful for athletes to do altitude contrast training.

The invention claimed is:

1. An apparatus for providing controlled concentration of inhalation-air to enhance adaptive response of a user's body, the apparatus comprising:
an air-reservoir for storing the inhalation-air, the air-reservoir comprising:
a first air chamber to store a first concentration of the inhalation-air ambient pressure, wherein the first concentration has a mixture of air with a first partial pressure of oxygen;
a second air chamber to store a second concentration of the inhalation-air at ambient pressure, wherein the second concentration has a mixture of air with a second partial pressure of oxygen;
wherein an interior portion of said air-reservoir is a material impervious to inhalation air and does not give off chemicals;
a control unit to control the concentration of the inhalation-air, the control unit receiving air from the air-reservoir and transferring the inhalation-air to the user, the control unit further comprising:
a housing that receives the inhalation-air from the air-reservoir;
a first duct protruding from the housing and configured with the first air chamber to supply the first concentration of inhalation-air to the housing;
a second duct protruding from the housing and configured with the second air chamber to supply the second concentration of inhalation-air to the housing;
a third duct protruding from the housing to transfer the inhalation-air from the housing to the user; and
a valve configured to control the flow of inhalation-air from at least one of the duct and the second duct to the housing; and
a switch unit that positions the valve to selectively open and close the first and second ducts for regulating flow of inhalation-air from the air-reservoir to the housing.

2. The apparatus according to claim 1, where the switch unit further comprises:
a cable that positions the valve; and
a mechanical switch having a first position that allows the housing to receive the inhalation-air from the first chamber; and a second position that allows the housing to receive the inhalation-air from the second chamber.

3. The apparatus according to claim 1, wherein the switch unit further comprises:
a solenoid that positions the valve; and
an electrical switch having a first position that allows the housing to receive the inhalation-air from the first chamber; and a second position that allows the housing to receive the inhalation-air from the second chamber.

4. The apparatus according to claim 1 further comprising: plurality of filter units, wherein at least one of the filter units is attached to the first duct and at least one of the filter units is attached to the second duct to filter the inhalation-air passing to the user.

5. The apparatus according to claim 1, wherein the housing further comprises:
a first strip attached on a right side of the second duct to maintain the position of the valve;
a second strip in between the first duct and the second duct to maintain the position of the valve;
a third strip attached on a left side of the first duct to maintain the position of the valve.

6. An apparatus for altitude contrast training to a user comprising:
an air-reservoir to store inhalation-air comprising:
a first air chamber that stores a first concentration of inhalation-air; at ambient pressure, the first concentration having a mixture of air with a first partial pressure of oxygen; and a second air chamber that stores a second concentration of inhalation-air at ambient pressure, the second concentration having a mixture of air with second partial pressure of oxygen;

wherein an interior portion of said air-reservoir is a material impervious to inhalation air and does not give off chemicals;

a mask to transfer the inhalation-air to the users for facilitating breathing;

a control unit to control the flow of inhalation-air from the air-reservoir to the masks, the control unit comprising:

a housing that receives the inhalation-air from the air-reservoir;

a first duct protruding from the housing and configured with the first air chamber to supply the first concentration of inhalation-air to the housing;

a second duct protruding from the housing and configured with the second air chamber to supply the second concentration of inhalation-air to the housing;

a third duct protruding from the housing to transfer the inhalation-air from the housing to the user; and a valve configured to control the flow of inhalation-air from at least one of the duct and the second duct to the housing;

a switch unit that positions the valve to selectively open and close the first and second ducts for regulating flow of inhalation-air from the air-reservoir to the housing; and one or more tubular conduits attached to the third duct to transfer inhalation air from the housing to the mask.

7. The apparatus according to claim 6, where the switch unit further comprises:

a cable that positions the valve; and a mechanical switch having a first position that allows the housing to receive the inhalation-air from the first chamber; and a second position that allows the housing to receive the inhalation-air from the second chamber.

8. The apparatus according to claim 6, wherein the switch unit further comprises:

a solenoid that positions the valve; and an electrical switch having a first position that allows the housing to receive the inhalation-air from the first chamber; and a second position that allows the housing to receive the inhalation-air from the second chamber.

9. The apparatus according to claim 6 further comprising: plurality of filter units, wherein at least one of the filter units is attached to the first duct and at least one of the filter units is attached to the second duct to filter the inhalation-air passing to the user.

10. The apparatus according to claim 6, wherein the housing comprises:

a first strip attached on a right side of the second duct to maintain the position of the valve;

a second strip in between the first duct and the second duct to maintain the position of the valve;

a third strip attached on a left side of the first duct to maintain the position of the valve.

11. The apparatus according to claim 6 wherein the first air chamber stores high oxygen concentration inhalation-air.

12. The apparatus according to claim 6 wherein the second air chamber stores low oxygen concentration inhalation-air.

13. The apparatus according to claim 6 wherein the air-reservoir is formed of a low-oxygen-permeability-material for accumulating oxygen in an undiluted form.

14. The apparatus according to claim 6 wherein the air-reservoir further comprising comprises a seam to separate the first air chamber from the second air chamber.

* * * * *